United States Patent [19]

Chang

[11] Patent Number: 5,912,003
[45] Date of Patent: Jun. 15, 1999

[54] SPRAY-TYPE INSECTICIDAL PAINT AND MANUFACTURING PROCESS THEREOF

[75] Inventor: Bong-suk Chang, Seoul, Rep. of Korea

[73] Assignee: Kukbo Pharma Co., Ltd., Chungcheongbuk-do, Rep. of Korea

[21] Appl. No.: 08/799,420

[22] Filed: Feb. 12, 1997

[51] Int. Cl.$^6$ .................................................. A01N 25/00
[52] U.S. Cl. .............................................. 424/405; 424/84
[58] Field of Search ............................... 424/84, 405, 407

[56] References Cited

U.S. PATENT DOCUMENTS

| | | | |
|---|---|---|---|
| 4,851,218 | 7/1989 | Hildebrandt et al. | 424/84 |
| 5,466,458 | 11/1995 | Martin et al. | 424/405 |
| 5,527,823 | 6/1996 | Martin et al. | 514/521 |

OTHER PUBLICATIONS

Lomer, CJ. et al: Tests of Agrochemicals & Cultivars 11 : Oct. 11, 1990.
Jain S. et al. Pesticides 23(11):21–24, 1989.
Yada, AK. et al. Helvetica Chimica Acta : 67: 1698–1701, 1984.

*Primary Examiner*—Sheela Huff
*Attorney, Agent, or Firm*—Birch, Stewart, Kolasch & Birch, LLP

[57] ABSTRACT

The present invention provides spray-type insecticidal paint which has long lasting insecticidal effects by contact against various insects but is not harmful to human and warm-blooded animals, containing 0.1–2.5 Wt % of a pyrethroid insecticide, 5–10 Wt % of organic acrylic resin, 0.01–0.1 Wt % of an insect attractant, 30–60 Wt % of a propellent and 30–50 Wt % of solvent, and manufacturing process thereof.

11 Claims, No Drawings

SPRAY-TYPE INSECTICIDAL PAINT AND MANUFACTURING PROCESS THEREOF

DETAILED DESCRIPTION OF THE INVENTION

The present invention relates to spray-type insecticidal paint and manufacturing process thereof. Especially, the present invention relates to the spray-type insecticidal paint which contains a main insecticidal ingredient selected from pyrethroid insecticides such as delta-methrine, permethrine, cypermethrine; an insect attractant selected from propyl cyclohexylacetate for roaches, Z-9-tricosene for flies and methyl 4-methyl-pyrrole-2-carboxylate for ants; usual resin; propellent and solvent; and manufacturing process thereof.

The conventional ways of control of insects have been made with spray-type insecticidal paints which consist of an insecticidal ingredient, solvents and propellent gas and is filled into a metal container in the form of compressed gaseous mixtures of ingredients mentioned above.

A manufacturing process for spray-type insecticidal paint that shows its insecticidal effects by contact is described in the French patent Nos 1,050,895 and 2,593,821. In said French patents, the spray-type paint is designed so that the insecticidal action is effected by forming a thin porous film due to the polarity of an ingredient of the composition ingredients after drying and then by migration of the insecticidal ingredient toward the surface by the surface tension of the base.

The French patent No. 7139852 discloses a method for manufacturing insecticidal varnish acting by contact, which can be applied on the papered wall or wall decoration panelling materials. According to the method described, the insecticidal solution is intended to be sprayed on paper hanged wall or wall decoration panelling materials by dilution it at 1–12% in the organic solvent at the temperature of 80° C.

The disadvantage of these inventions cited above is that the spray-type paint and varnish incorporated with insecticide are not positive in exterminating pests such as roaches, flies, ants, etc. and the extermination is achieved only when the pests walk across the treated areas or when they ingest the paint or varnish by gnawing off. Thus the varnish and paint disclosed in patents mentioned above, that act by formation of a thin porous film containing the insecticidal ingredient are thought to be of a very negative method.

The present inventors have found that spray-type insecticidal paint which contains a pyrethroid insecticide, that has less hazard to human and domestic animals and on the other hand shows lethal effects on the target pests, and, in addition, an attractant for the pests has markedly increased effects for killing the pests by attracting the pests onto the insecticide.

Accordingly, an object of the present invention is to provide spray-type insecticial paint which contains a insecticidal ingredient selected from delta-methrine, permethrine and cypermethrine that belong to the pyrethroids; an insect attractant selected from propyl cyclohexylacetate for roaches, Z-9-tricosene for flies and methyl 4-methyl-pyrrole-2-carboxylate for ants; usual resin; propellent and solvent.

Another object of the present invention is to provide manufacturing process of the spray-type insecticidal paint above.

Pyrethroids insecticides have the properties to decompose when exposed to air, sun light and heat and thus cause no environmental pollution. They show the residual efficacy long-lasting for a set period and thus have no need of frequent treatment thereof, whereby it is possible to save economic losses. The pyrethroid insecticides cause fatal damages by contact to cold-blooded animals and pest insects, but exposure thereto is not harmful to human, domestic animals and pets is not harmful.

Solvents that can be used in this invention include, for example, 1,4-dioxane, 1,1,1-trichloroethane, methanol and ethanol.

Spray-type insecticidal paints according to the present invention contains preferably 0.1–2.5 Wt % of a pyrethroid insecticide that acts by contact, 5–10 Wt % of organic acrylic resin, 0.01–0.1 Wt % of an insect attractant, 30–60 Wt % of a propellent and 30–50 Wt % of solvent. The spray-type insecticidal paints may be manufactured by filling the ingredients above into a metal container that is designed to hold the compressed gaseous mixture according to the usual manufacturing process.

Following Examples are intended to further illustrate the present invention without limiting its scope.

EXAMPLE 1

| | |
|---|---|
| Delta-methrine | 0.1–2.5 g |
| Organic acrylic resin | 5–10 g |
| Propyl cyclohexyl acetate | 0.01–0.1 g |
| LPG(Propellent) | 50 g |
| 1,4-dioxane | 8 g |
| 1,1,1-trichloroethane | 1.5 g |
| Methanol | 10 g |
| Ethanol | 25 g |

A spray-type insecticidal paint was prepared by filling the above ingredients in the metal container that is designed to hold the compressed gaseous substance according to a usual manufacturing process for the spray-type insecticides.

EXAMPLE 2

| | |
|---|---|
| Delta-methrine | 0.1–2.5 g |
| Organic acrylic | 5–10 g |
| Z-9-Tricosene | 0.01–0.1 g |
| LPG(propellent) | 50 g |
| 1.4-dioxane | 8 g |
| 1,1,1-trichloroethane | 1.5 g |
| Methanol | 10 g |
| Ethanol | 25 g |

A spray-type insecticidal paint was prepared by filling the above ingredients in the metal container that is designed to hold the compressed gaseous substance, according to a usual manufacturing process for the spray-type insecticides.

EXAMPLE 3

| | |
|---|---|
| Delta-methrine | 0.1–2.5 g |
| Organic acrylic resin | 5–10 g |
| Methyl 4-methyl-pyrrole-2-carboxylate | 0.01–2.5 g |
| LPG(propellent) | 50 g |
| 1,4-dioxane | 8 g |
| 1,1,1-trichloroethane | 1.5 g |
| Methanol | 10 g |
| Ethanol | 25 g |

A spray-type insecticidal paint was prepared by filling the above ingredients in the metal container that is designed to hold the compressed gaseous substance according to a usual manufacturing process for the spray-type insecticides.

EXAMPLE 4

| | |
|---|---|
| Permethrine | 0.1–2.5 g |
| Organic acrylic resin | 5–10 g |
| Propyl cyclohexyl acetate | 0.01–01 g |
| LPG(propellent) | 50 g |
| 1,4-dioxane | 8 g |
| 1,1,1-trichloroethane | 1.5 g |
| Methanol | 10 g |
| Ethanol | 25 g |

A spray-type insecticidal paint was prepared by filling the above ingredients in the metal container that is designed to hold the compressed gaseous substance according to a usual manufacturing process for the spray-type insecticides.

EXAMPLE 5

| | |
|---|---|
| Permethrine | 0.1–2.5 g |
| Organic acrylic resin | 5–10 g |
| Z-9-tricosene | 0.01–0.1 g |
| LPG(propellent) | 50 g |
| 1,4-dioxane | 8 g |
| 1,1,1-trichloroethane | 1.5 g |
| Methanol | 10 g |
| Ethanol | 25 g |

A spray-type insecticidal paint was prepared by filling the above ingredients in the metal container that is designed to hold the compressed gaseous substance according to a usual manufacturing process for the spray-type insecticides.

EXAMPLE 6

| | |
|---|---|
| Permethrine | 0.1–2.5 g |
| Organic acrylic resin | 5–10 g |
| methyl 4-methyl-pyrrole-2-carboxylate | 0.01–0.1 g |
| LPG(propellent) | 50 g |
| 1,4-dioxane | 8 g |
| 1,1,1-trichloroethane | 1.5 g |
| Methanol | 10 g |
| Ethanol | 25 g |

A spray-type insecticidal paint was prepared by filling the above ingredients in the metal container that is designed to hold the compressed gaseous substance according to a usual manufacturing process for the spray-type insecticides.

EXAMPLE 7

| | |
|---|---|
| Cypermethrine | 0.1–2.5 g |
| Organic acrylic resin | 5–10 g |
| Propyl cyclohexyl acetate | 0.01–0.1 g |
| LPG(propellent) | 50 g |
| 1,4-dioxane | 8 g |
| 1,1,1-trichloroethane | 1.5 g |
| Methanol | 10 g |
| Ethanol | 20 g |

A spray-type insecticidal paint was prepared by filling the above ingredients in the metal container that is designed to hold the compressed gaseous substance according to a usual manufacturing process for the spray-type insecticides.

EXAMPLE 8

| | |
|---|---|
| Cypermethrine | 0.1–2.5 g |
| Organic acrylic resin | 5–10 g |
| Z-9-tricosene | 0.01–0.1 g |
| LPG(propellent) | 50 g |
| 1,4-dioxane | 8 g |
| 1,1,1-trichloroethane | 1.5 g |
| Methanol | 10 g |
| Ethanol | 25 g |

A spray-type insecticidal paint was prepared by filling the above ingredients in the metal container that is designed to hold the compressed gaseous substance according to a usual manufacturing process for the spray-type insecticides.

EXAMPLE 9

| | |
|---|---|
| Cypermethrine | 0.1–2.5 g |
| Organic acrylic resin | 5–10 g |
| Methyl 4-methylpyrrole-2-carboxylate | 0.01–0.1 g |
| LPG(propellent) | 50 g |
| 1,4-dioxane | 8 g |
| 1,1,1-trichloroethane | 1.5 g |
| Methanol | 10 g |
| Ethanol | 25 g |

A spray-type insecticidal paint was prepared by filling the above ingredients in the metal container that is designed to hold the compressed gaseous substance according to a usual manufacturing process for the spray-type insecticides.

Comparative example: Manufacturing of an insecticidal Varnish (Maker A)

| | |
|---|---|
| Natural or synthetic resin | 11 g |
| Linseed oil | 30 g |
| Anhydrous castor oil | 7 g |
| Mineral or Vegetable oil | 35 g |
| Insecticide(Pyrethrin) | 4 g |

A insecticidal varnish was prepared by a method according to a usual manufacturing process for the varnishes.

Example of experiment

Experimental tests for insecticidal efficacy of the present spray-type insecticidal paints against roaches and flies were carried out and compared with that of the insecticidal varnish prepared by the comparative example using a conventional method in this field, and the results are shown in Table 1 and Table 2.

TABLE 1

Comparative insecticidal efficacy on cockroach.

| Days after painting & spraying | Period of Experiment | No. of Experiment | Product of Maker A No. of Death | Product of Maker A Mortality | Insecticide from Ex. 1 No. of Death | Insecticide from Ex. 1 Mortality |
|---|---|---|---|---|---|---|
| 1 | 30 min | 50 | 0 | 0 | 0 | 0 |
|   | 1 hr | 50 | 8 | 16 | 24 | 48 |
|   | 24 hr | 50 | 50 | 100 | 50 | 100 |
| 20 | 30 min | 50 | 0 | 0 | 0 | 0 |
|   | 1 hr | 50 | 0 | 0 | 12 | 48 |
|   | 24 hr | 50 | 43 | 86 | 50 | 100 |
| 30 | 30 min | 50 | 0 | 0 | 0 | 0 |
|   | 1 hr | 50 | 0 | 0 | 8 | 16 |
|   | 24 hr | 50 | 36 | 72 | 47 | 94 |
| 60 | 24 hr | 50 | 28 | 56 | 44 | 88 |

TABLE 2

Comparative insecticidal efficacy on fly.

| Days after painting & spraying | Period of Experiment | No. of Experiment | Product of Maker A | | Insecticide from Ex. 2 | |
|---|---|---|---|---|---|---|
| | | | No. of Death | Mortality | No. of Death | Mortality |
| 1 | 30 min | 50 | 50 | 100 | 50 | 100 |
| | 1 hr | 50 | 50 | 100 | 50 | 100 |
| | 24 hr | 50 | 50 | 100 | 50 | 100 |
| 20 | 30 min | 50 | 41 | 0 | 0 | 0 |
| | 1 hr | 50 | 48 | 0 | 12 | 48 |
| | 24 hr | 50 | 50 | 86 | 50 | 100 |
| 30 | 30 min | 50 | 35 | 0 | 0 | 0 |
| | 1 hr | 50 | 43 | 0 | 8 | 16 |
| | 24 hr | 50 | 48 | 72 | 47 | 94 |
| 60 | 30 min | 50 | 27 | 54 | 45 | 90 |
| | 1 hr | 50 | 34 | 68 | 48 | 96 |
| | 24 hr | 50 | 44 | 88 | 50 | 100 |

Comparative experiments for pesticidal efficacy on roach is as shown in Table 1, and the product of Maker A shows decrease in the numbers of death from 30 days after the treatment, whereas the spray-type paint of the present invention continues to have good control and long residual effects.

The comparative experiment for pesticidal efficacy and residual efficacy on fly is as shown in Table 2, which likewise shows that while the product of Maker A steeply decreases in the numbers of death of fly, the spray-type paint of the present invention continues to have good control and long duration of effects even 60 days after the treatment.

What is claimed is:

1. An insecticidal paint composition, comprising:
   0.1–2.5 percent by weight of a pyrethroid insecticide,
   5–10 percent by weight of an acrylic resin,
   0.01–0.1 percent by weight of an insect attractant,
   30–60 percent by weight of a propellant, and
   30–50 percent by weight of a solvent.

2. The composition of claim 1, wherein said pyrethroid insecticide is selected from the group consisting of delta-methrine, permethrine and cypermethrine.

3. The composition of claim 1, wherein said insect attractant is selected from the group consisting of propyl cyclohexylacetate, Z-9-tricosene and 4-methylpyrrol-2-carboxylate.

4. The composition of claim 1, wherein said solvent is selected from the group consisting of 1,4-dioxane, 1,1,1-trichloroethane, methanol and ethanol.

5. An insecticidal paint composition, comprising:
   0.1–2.5 percent by weight of a pyrethroid insecticide, which is selected from the group consisting of delta-methrine, permethrine and cypermethrine;
   5–10 percent by weight of an acrylic resin;
   0.01–0.1 percent by weight of an insect attractant, which is selected from the group consisting of propyl cyclohexylacetate, Z-9-tricosene and 4-methylpyrrol-2-carboxylate;
   30–60 percent by weight of a propellant; and
   30–50 percent by weight of a solvent, which is selected from the group consisting of 1,4-dioxane, 1,1,1-trichloroethane, methanol and ethanol.

6. A container containing the composition of claim 1.

7. A method of controlling insects comprising spraying the insecticidal paint composition according to claim 1 on an area in need thereof.

8. The method of claim 7, wherein said pyrethroid insecticide is selected from the group consisting of delta-methrine, permethrine and cypermethrine.

9. The method of claim 7, wherein said insect attractant is selected from the group consisting of
   propyl cyclohexylacetate, Z-9-tricosene and 4-methylpyrrol-2-carboxylate.

10. The method of claim 7, wherein said solvent is selected from the group consisting of
    1,4-dioxane, 1,1,1-trichloroethane, methanol and ethanol.

11. The method of claim 7, comprising:
    0.1–2.5 percent by weight of a pyrethroid insecticide, which is selected from the group consisting of delta-methrine, permethrine and cypermethrine;
    5–10 percent by weight of an acrylic resin;
    0.01–0.1 percent by weight of an insect attractant, which is selected from the group consisting of propyl cyclohexylacetate, Z-9-tricosene and 4-methylpyrrol-2-carboxylate;
    30–60 percent by weight of a propellant; and
    30–50 percent by weight of a solvent wherein said solvent is selected from the group consisting of 1,4-dioxane, 1,1,1-trichloroethane, methanol and ethanol.

* * * * *